(12) United States Patent
Liao et al.

(10) Patent No.: US 10,363,327 B2
(45) Date of Patent: *Jul. 30, 2019

(54) LUMINAIRE WITH WHITE LIGHT LEDS AND UV LEDS FOR LIGHTING AND DISINFECTION

(71) Applicant: RayVio Corporation, Hayward, CA (US)

(72) Inventors: Yitao Liao, Redwood City, CA (US); Douglas A. Collins, Hayward, CA (US); Theodore J. de Jony, Campbell, CA (US); Robert C. Walker, Redwood City, CA (US); Elaine Taylor, Hayward, CA (US)

(73) Assignee: RayVio Corporation, Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/200,190

(22) Filed: Nov. 26, 2018

(65) Prior Publication Data

US 2019/0091358 A1    Mar. 28, 2019

Related U.S. Application Data

(63) Continuation of application No. 15/188,573, filed on Jun. 21, 2016, now Pat. No. 10,166,309, which is a
(Continued)

(51) Int. Cl.
*A61L 2/10* (2006.01)
*H05B 33/08* (2006.01)
(Continued)

(52) U.S. Cl.
CPC ............... *A61L 2/10* (2013.01); *C02F 1/008* (2013.01); *C02F 1/325* (2013.01);
(Continued)

(58) Field of Classification Search
CPC ..... A61L 2/10; A61L 2/24; A61L 9/20; A61L 2202/14; A61L 2202/25; A61L 2209/12; A61L 2209/111
See application file for complete search history.

(56) References Cited

U.S. PATENT DOCUMENTS 5,621,516 A    4/1997  Shinzaki et al.
8,114,346 B2   2/2012  Hyde et al.
(Continued)

OTHER PUBLICATIONS

Indigo-Clean, "A Light Fixture that Reduces Harmful Bacteria", accessed Jun. 20, 2016.
(Continued)

*Primary Examiner* — Wyatt A Stoffa
(74) *Attorney, Agent, or Firm* — Patent Law Group LLP; Brian D. Ogonowsky

(57) ABSTRACT

A variety of applications for UV LEDs that are integrated into a system are described, where the UV light is used for disinfection of air or surfaces, or used to detect the scattering light by particles, or used for skin treatment. In one embodiment, a ceiling luminaire includes a sensor for detecting the presence of people in the room. The luminaire contains a first set of LEDs for generating white light, for illumination, and a second set of LEDs for generating UV light for disinfecting the room. When the sensor detects that no people are in the room, the system automatically controls the UV LEDs to turn on to disinfect the room. The white light LEDs may be independently controlled with a dimmer.

17 Claims, 10 Drawing Sheets

Related U.S. Application Data continuation of application No. 14/661,546, filed on Mar. 18, 2015, now abandoned.

(51) Int. Cl.
  *C02F 1/00*    (2006.01)
  *C02F 1/32*    (2006.01)

(52) U.S. Cl.
  CPC .... *H05B 33/0854* (2013.01); *C02F 2201/326* (2013.01); *C02F 2201/3222* (2013.01); *C02F 2201/3224* (2013.01); *C02F 2201/3227* (2013.01); *C02F 2201/3228* (2013.01); *C02F 2209/001* (2013.01); *C02F 2209/44* (2013.01); *C02F 2303/04* (2013.01); *G06F 2203/0338* (2013.01)

(56) References Cited

U.S. PATENT DOCUMENTS

| | | | |
|---|---|---|---|
| 9,370,600 B1* | 6/2016 | DuPuis | A61L 9/20 |
| 10,166,309 B2* | 1/2019 | Liao | A61L 2/10 |
| 2007/0205382 A1 | 9/2007 | Gaska et al. | |
| 2007/0258852 A1* | 11/2007 | Hootsmans | A61L 2/088 |
| | | | 422/24 |
| 2009/0004046 A1* | 1/2009 | McEllen | A61L 9/20 |
| | | | 422/2 |
| 2009/0117001 A1 | 5/2009 | Hyde | |
| 2009/0191100 A1* | 7/2009 | Deal | A61L 2/10 |
| | | | 422/105 |
| 2009/0280035 A1* | 11/2009 | Koudymov | A23L 3/28 |
| | | | 422/108 |
| 2010/0003165 A1* | 1/2010 | McEllen | A61L 9/20 |
| | | | 422/4 |
| 2011/0256019 A1 | 10/2011 | Gruen | |
| 2012/0127296 A1 | 5/2012 | Oguchi | |
| 2012/0156094 A1* | 6/2012 | Gordon | A61L 2/10 |
| | | | 422/24 |
| 2012/0199005 A1* | 8/2012 | Koji | A61L 9/205 |
| | | | 96/224 |
| 2012/0315186 A1* | 12/2012 | Davis | A61L 2/10 |
| | | | 422/24 |
| 2014/0300581 A1* | 10/2014 | Aurongzeb | G06F 1/1601 |
| | | | 345/175 |
| 2015/0064065 A1 | 3/2015 | Kreitenberg | |
| 2015/0118107 A1* | 4/2015 | Sunkara | A61L 2/24 |
| | | | 422/24 |
| 2015/0335246 A1* | 11/2015 | Rains, Jr. | F21V 23/003 |
| | | | 362/231 |
| 2016/0030610 A1* | 2/2016 | Peterson | A61L 2/084 |
| | | | 362/84 |
| 2016/0175475 A1* | 6/2016 | DuPuis | A61L 9/20 |
| | | | 250/432 R |
| 2016/0317690 A1* | 11/2016 | Dayton | A61L 2/26 |
| 2017/0049915 A1* | 2/2017 | Brais | H05B 37/0227 |

OTHER PUBLICATIONS

Lynne E. Murdoch et al., "Bactericidal Effects of 405 nm Light Exposure Demonstrated by Inactivation of *Escherichia, Salmonells, Shigella, Listeria*, and *Mycobaterium* Species in Liquid Suspensions and on Exposed Surfaces" The Scientific World Journal, vol. 2012, article ID 137805, 8 pages.

Michelle MacLean, "Inactivation of Bacterial Pathogens Following Exposure to Light from a 405-Nanometer Light-Emitting Diode Array", Applied and Environmental Microbiology, Feb. 2009, pp. 1932-1937.

T.J. Nelson et al., "Leaky Lightguide/LED Row-Backlight, Column-Shutter Display," IEEE Trans. on Electronic Devices, vol. 38, No. 11, 1991, pp. 2567-2569.

Tru-D Smartuvc, "Tru-D Smart UVC", accessed Jun. 20, 2016.

XENEX Disinfection Services, "High-energy, Full Spectrum 1M Pulsed Xenon ultraviolet light, known as UV-C, is extremely fast and effective at reducing microbial load".

\* cited by examiner

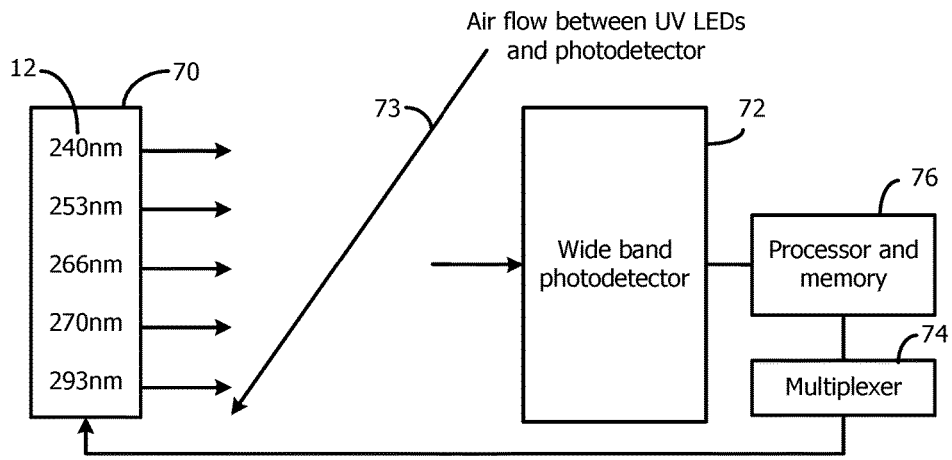
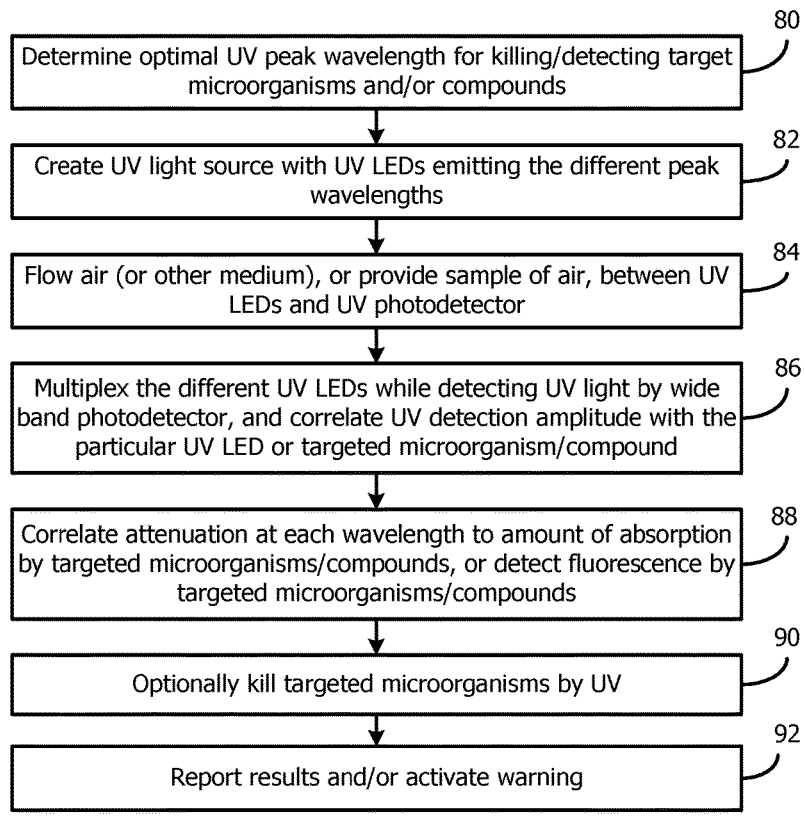

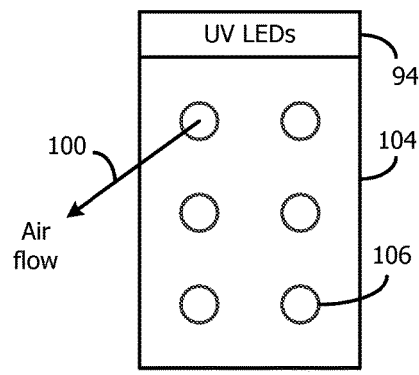
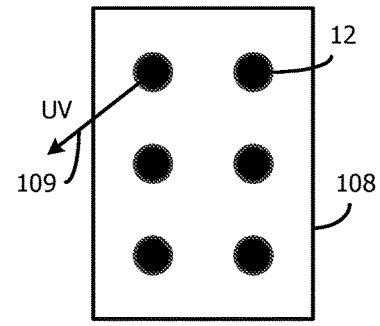
Fig. 8　　　　　Fig. 9
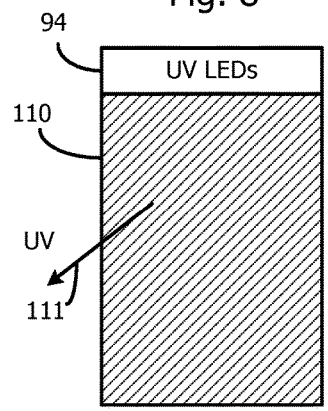
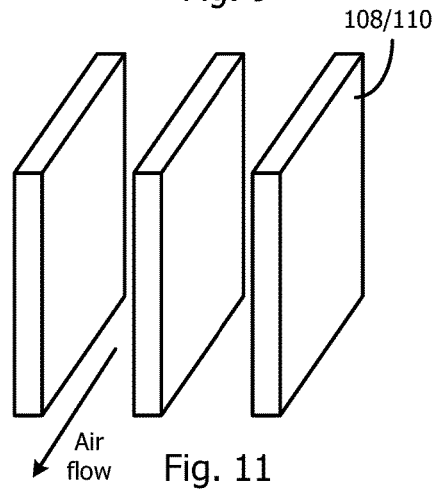
Fig. 10　　　　　Fig. 11
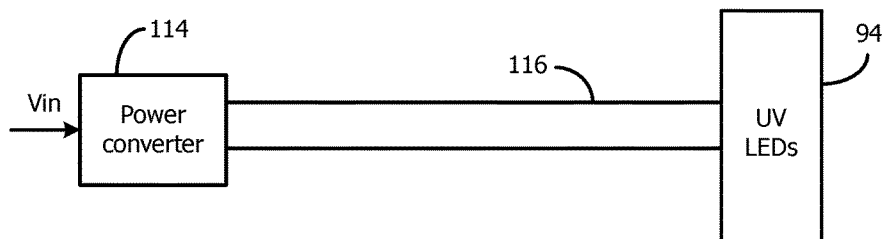
Fig. 12

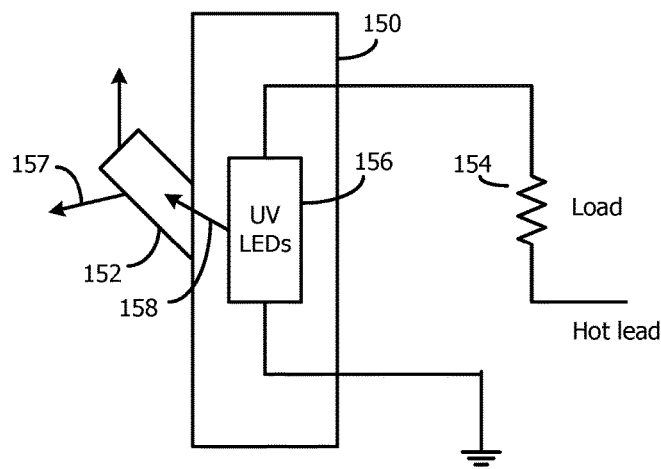
Fig. 16
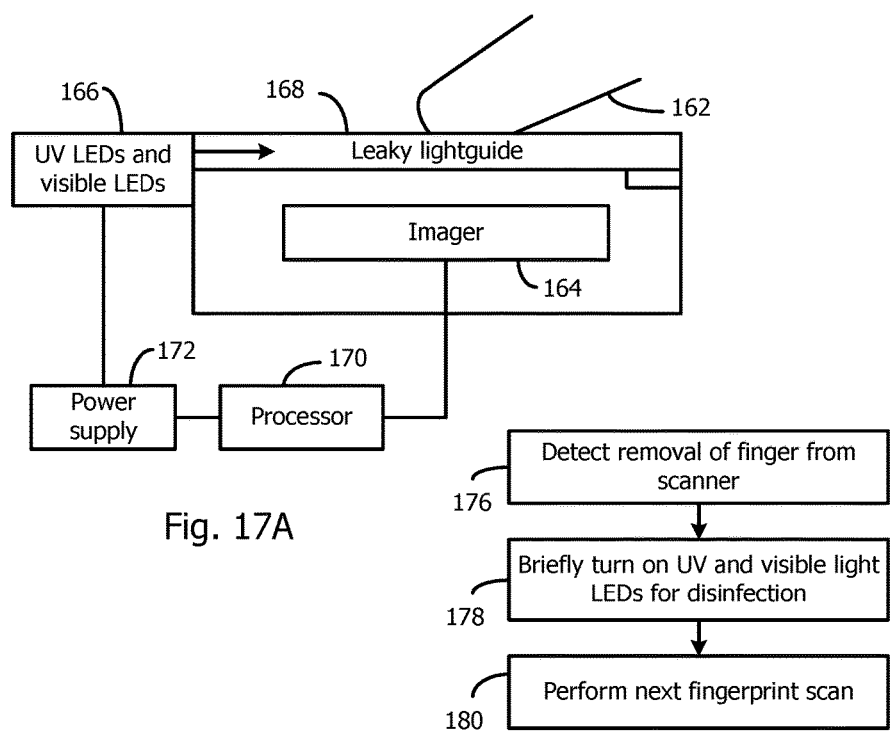
Fig. 17A
Fig. 17B

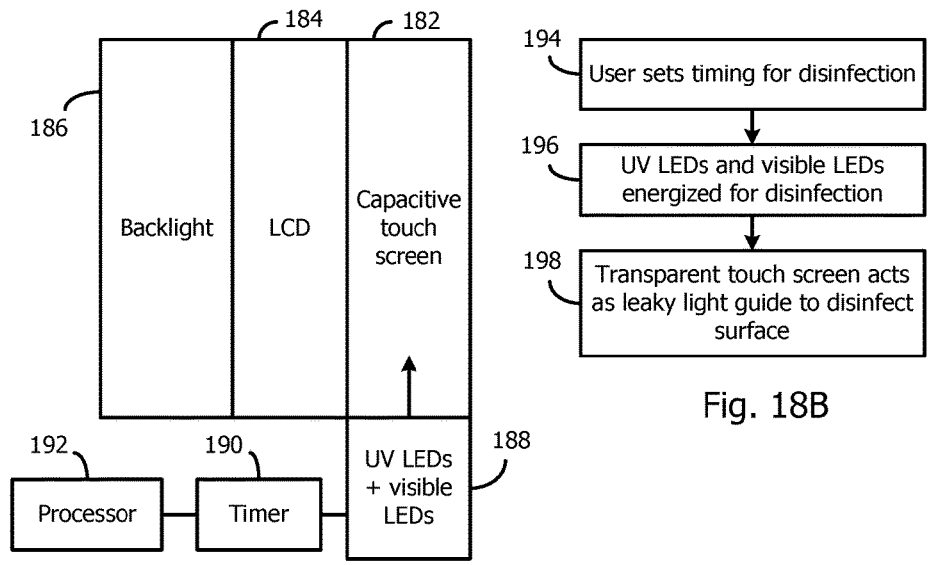
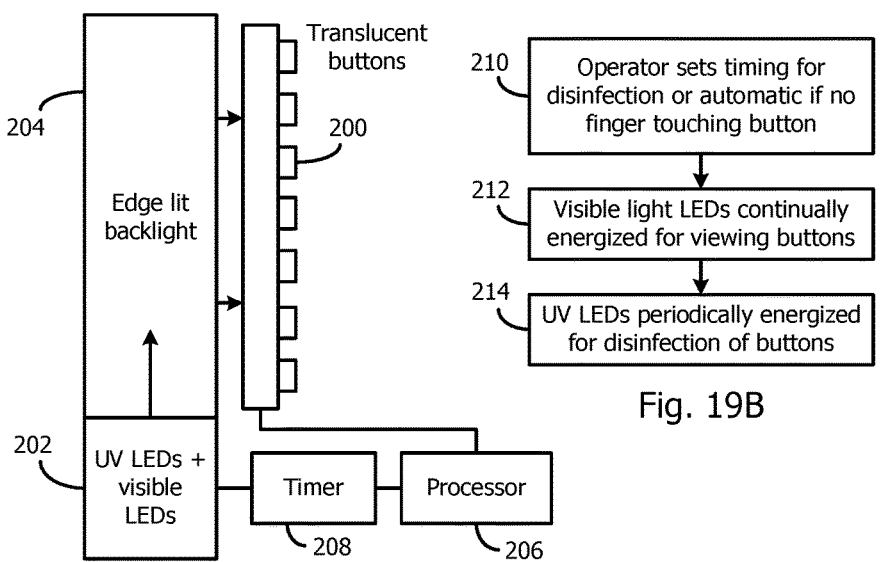

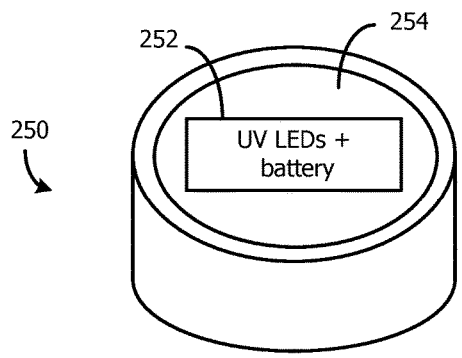
Fig. 22
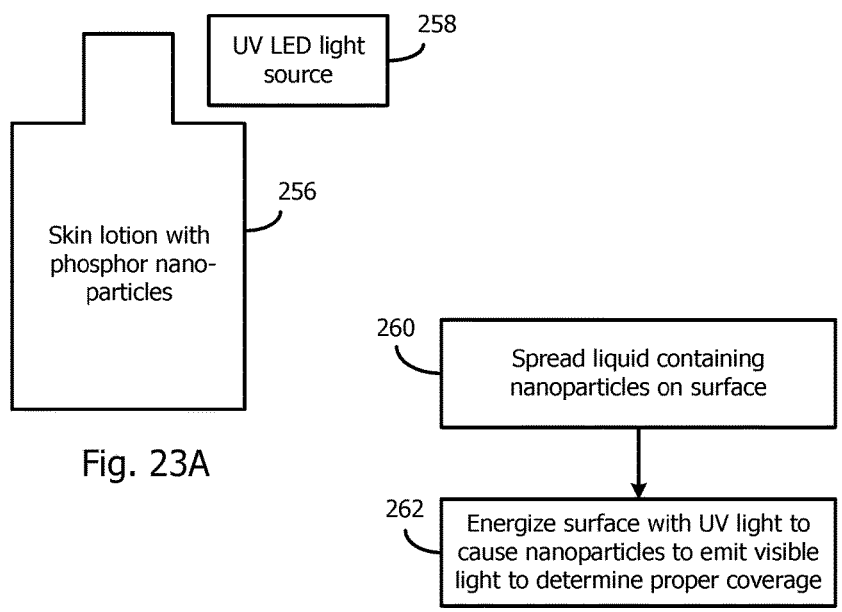
Fig. 23A
Fig. 23B

LUMINAIRE WITH WHITE LIGHT LEDS AND UV LEDS FOR LIGHTING AND DISINFECTION

CROSS-REFERENCE TO RELATED APPLICATIONS

This is a continuation of U.S. application Ser. No. 15/188,573, filed Jun. 21, 2016, which is a continuation of U.S. application Ser. No. 14/661,546, filed Mar. 18, 2015, assigned to the present assignee and incorporated herein by reference.

FIELD OF INVENTION

The present invention relates to various applications of ultraviolet (UV) light emitting diodes (LEDs) for disinfecting air, water, and surfaces.

BACKGROUND

Useful UV light for disinfecting air, water, and surfaces is generally considered to be in the range between 400 nm and 100 nm. Such UV may break down molecular bonds within DNA, which kills or inactivates microorganisms. The specific bands of UV wavelengths for effectively killing various types of organisms have been extensively studies and are known. For example, the wavelength of about 254 nm has been determined to be optimal for killing common microorganisms found in water and air, and the wavelength of 293 nm is optimal for killing certain other types of microorganisms. These optimal wavelengths are in the UVB range (315 nm-280 nm) and UVC range (280 nm-100 nm). Such disinfection is typically combined with filtration to filter out larger organisms. The UV exposure to perform such disinfection is typically in the range of 2000-8000 $uW \cdot s/cm^2$.

Currently, by far the most common UV emitters for disinfection are mercury-vapor lamps and xenon lamps. Such lamps emit a very wide range of UV wavelengths, and the vast majority of the emitted wavelengths (an associated power) have no effect on killing microorganisms. Such emitted wavelengths waste energy and can be harmful to humans over long exposure periods. Such lamps also need a high voltage power supply, which can create safety issues. The ideal UV emitter is one that generates a very narrow range of UV wavelengths, where the peak emitted wavelength is that which is the most efficient at killing the microorganisms of interest. UV LEDs approach such an ideal UV emitter since almost all optical power is in a very narrow band of wavelengths, and the peak wavelength can be controlled by the materials used in the active layer of the LED.

UV LEDs useful for disinfection are in their infancy, and commercially available UV LEDs that emit in the UVB and UVC wavelengths emit low power (e.g., less than 10 mW), are very inefficient, and are very expensive. The present assignee has developed much more powerful UV LEDs in this wavelength range, and a detailed fabrication process for forming such UV LEDs is described in U.S. patent application Ser. No. 14/635,903, filed Mar. 2, 2015, assigned to the present assignee and incorporated herein by reference.

It is inevitable that the costs of UV LEDs with a selectable and optimal peak emission within the UVB and UVC range will come down and the power levels per UV LED will greatly increase. Therefore, using such UV LEDs instead of relatively large mercury-vapor or xenon lamps will become much more cost-effective for disinfection.

Thus, novel designs for various disinfection systems using UVB and UVC LEDs are needed that make use of the added flexibility that small LEDs offer.

SUMMARY

The present disclosure describes various novel uses for UVB and UVC LEDs for disinfection. By using UV LEDs, versus relatively large mercury-vapor or xenon lamps, the UV wavelength of interest can be more efficiently coupled to the medium to be disinfected. Additionally, some of the applications described herein use the smaller wavelength of UV to detect smaller particles in an air flow.

Although a sufficient number of commercially available UVB and UVC LEDS may be used in the embodiments to supply the required UV exposure (e.g., >2000 $uW \cdot s/cm^2$), the assignee's new, more powerful UV LEDs will greatly reduce the costs needed to implement the present inventions.

Various systems employing UV LEDs described herein include:

UV LEDs for detecting very small unfiltered particles within an air flow;

Multiple UV LEDs with different peak wavelengths in a single system for killing different types of organisms and/or for detecting different types of organisms/compounds based on absorption;

Systems to more effectively couple UV LED light into air or water, such as using a fiber optic mesh, parallel light guide blades, or a light guide with holes;

UV LEDs coupled to optical fiber for medical applications, such as for disinfection during micro-surgery;

UV LEDs to detect fluorescent nanoparticles in blood;

Use of the inherent waveguiding properties of water to direct UV LED light, such as for disinfecting foods;

UV LEDs to disinfect surfaces touched by the public, such as ATM keys, keyboards, push buttons, light switches, handles, fingerprint sensor surfaces, touch screen surfaces, etc.

UV LEDs integrated into general illumination white light structures to disinfect air and surfaces in a room;

UV LEDs for skin treatment;

UV LEDs in a wearable device for generating vitamin D;

UV LEDs to determine the coverage of a liquid substance containing fluorescent particles.

Other applications are described.

BRIEF DESCRIPTION OF DRAWINGS

FIG. 4A illustrates a system that emits a plurality of narrow UV wavelength ranges for detecting particles and disinfecting the air in an air duct.

FIG. 4B is a flowchart describing the use of the system of FIG. 4A.

FIG. 8 illustrates an edge-lit light guide with holes to couple UV light to a medium flowing through the holes.

FIG. 9 illustrates a circuit board having mounted thereon an array of UV LEDs.

FIG. 10 illustrates an edge-lit light guide that is roughened to leak the UV light.

FIG. 11 illustrates UV-emitting flat panels in an air or water flow for disinfecting the medium.

FIG. 12 illustrates how the input voltage supply and the power converter for the UV LEDs may be remotely located.

FIG. 16 is a cross-sectional view of a light switch with internal UV LEDs for disinfecting a translucent switch lever.

FIG. 17A is a cross-sectional view of a fingerprint sensor using UV LEDs to supply UV light to a scanner surface to disinfect the surface.

FIG. 17B is a flowchart describing the used of the system of FIG. 17A.

FIG. 18A illustrates a display and touch screen system where UV LEDs are used to disinfect the surface of the touch screen.

FIG. 18B is a flowchart describing the use of the system of FIG. 18A.

FIG. 19A illustrates a system for disinfecting push-buttons using UV LEDs.

FIG. 19B is a flowchart describing the use of the system of FIG. 19A.

FIG. 22 illustrates a wristband for supplying UV light to the wearer's skin to generate vitamin D.

FIG. 23A illustrates a bottled liquid containing nanoparticles of a phosphor to visibly determine coverage when the applied liquid is energized by UV light.

FIG. 23B is a flowchart describing the use of the system of FIG. 23A.

Elements that are the same or equivalent are labeled with the same numerals.

DETAILED DESCRIPTION

Figure 1:
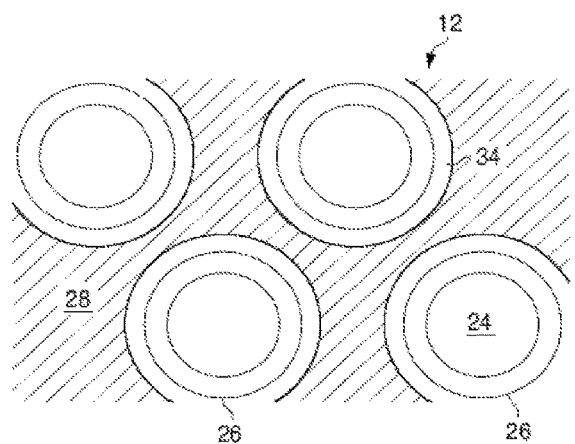
FIG. 1 is a top down view of a portion of an array of UV LEDs.
Figure 2:
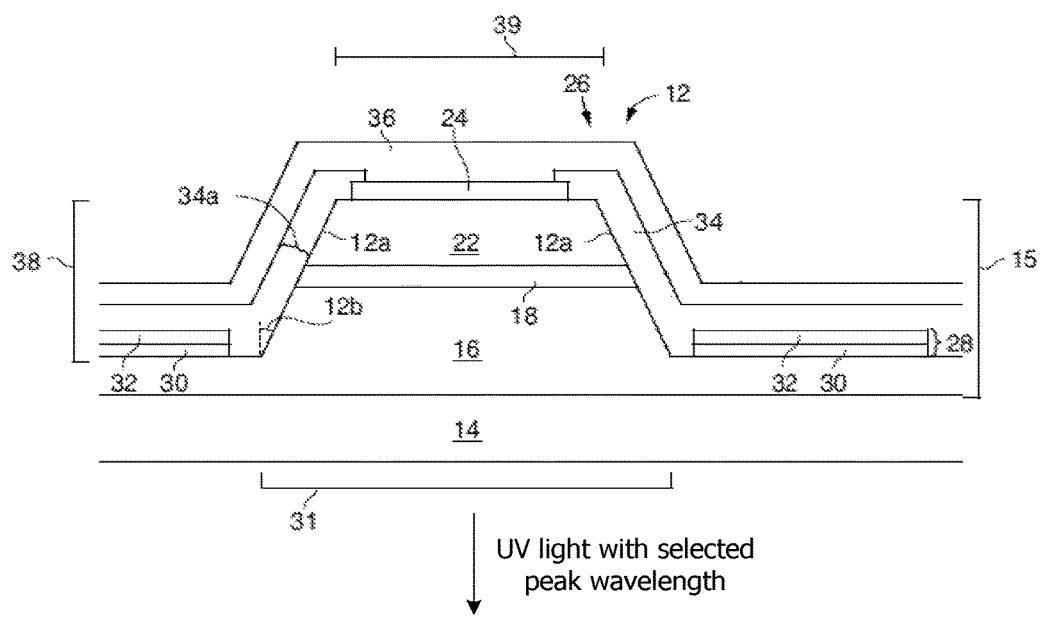
FIG. 2 is a bisected cross-sectional view of one of the UV LEDs in FIG. 1.

Commercially available UVA, UVB, and UVC LEDs may be used in the various embodiments for disinfection. FIGS. 1 and 2 are examples of the assignee's own UVB and UVC LEDs that may also be used. FIG. 1 is a top down view of a portion of an array of UV LEDs 12, and FIG. 2 is a bisected cross-section of a single UV LED 12. An integral two-dimensional array of UV LEDs is not required for the inventions, since individual segmented UV LEDs may also be used. A narrow strip of UV LEDs may be useful in some of the embodiments. Any number of UV LEDs can be employed in the embodiments depending on the desired optical power.

The UV LEDs are typically GaN-based, and commonly AlGaN. The active layers of the devices described herein may be configured to emit UVA (peak wavelength between 340 and 400 nm), UVB (peak wavelength between 290 and 340 nm), or UVC (peak wavelength between 210 and 290 nm) radiation.

The array of UV LEDs 12 is formed on a single substrate 14, such as a transparent sapphire substrate. Other substrates are possible. Although the example shows the UV LEDs 12 being round, they may have any shape, such as square. The light escapes through the transparent substrate, as shown in FIG. 2. The UV LEDs 12 may be flip-chips, where the anode and cathode electrodes face the printed circuit board, or a wire bond may be used for one or both electrodes.

All semiconductor layers are epitaxially grown over the substrate 14. An AlN or other suitable buffer layer (not shown) is grown, followed by an n-type region 16. The n-type region 16 may include multiple layers of different compositions, dopant concentrations, and thicknesses. The n-type region 16 may include at least one $Al_aGa_{1-a}N$ film doped n-type with Si, Ge and/or other suitable n-type dopants. The n-type region 16 may have a thickness from about 100 nm to about 10 microns and is grown directly on the buffer layer(s). The doping level of Si in the n-type region 16 may range from $1\times10^{16}$ cm$^{-3}$ to $1\times10^{21}$ cm$^3$. Depending on the intended emission wavelength, the AlN mole fraction "a" in the formula may vary from 0% for devices emitting at 360 nm to 100% for devices designed to emit at 200 nm.

An active region 18 is grown over the n-type region 16. The active region 18 may be either a single quantum well or multiple quantum wells (MQWs) separated by barrier layers. The quantum well and barrier layers contain $Al_xGa_{1-x}N/Al_yGa_{1-y}N$, wherein 0<x<y<1, x represents the AlN mole fraction of a quantum well layer, and y represents the AlN mole fraction of a barrier layer. The peak wavelength emitted by a UV LED is generally dependent upon the relative content of Al in the AlGaN quantum well active layer, which can be selected by the manufacturer.

A p-type region 22 is grown over the active region 18. Like the n-type region 16, the p-type region 22 may include multiple layers of different compositions, dopant concentrations, and thicknesses. The p-type region 22 includes one or more p-type doped (e.g. Mg-doped) AlGaN layers. The AlN mole fraction can range from 0 to 100%, and the thickness of this layer or multilayer can range from about 2 nm to about 100 nm (single layer) or to about 500 nm (multilayer). A multilayer used in this region can improve lateral conductivity. The Mg doping level may vary from $1\times10^{16}$ cm$^{-3}$ to $1\times10^{21}$ cm$^3$. A Mg-doped GaN contact layer may be grown last in the p-type region 22. The Mg doping level can vary from $1\times10^{16}$ cm$^{-3}$ to $1\times10^{21}$ cm$^{-3}$.

The semiconductor structure 15 is etched to form trenches between the UV LEDs 12 that reveal a surface of the n-type region 16. The sidewalls 12a and 12b of the UV LEDs 12 may be vertical or sloped. The height 38 of each UV LED 12 may be between 0.1-5 microns. The widths 31 and 39 at the bottom and top of each UV LED 12 may be at least 5 microns. Other dimensions may also be used.

Before or after etching the semiconductor structure 15 to form the trenches, a metal p-contact 24 is deposited and patterned on the top of each UV LED 12. The p-contact 24 may include one or more metal layers that form an ohmic contact, and one or more metal layers that form a reflector. One example of a suitable p-contact 24 includes a Ni/Ag/Ti multi-layer contact.

An n-contact 28 is deposited and patterned, such that n-contact 28 is disposed on the substantially flat surface of the n-type region 16 between the UV LEDs 12. The n-contact 28 may include a single or multiple metal layers. The n-contact 28 may include, for example, an ohmic n-contact 30 in direct contact with the n-type region 16, and an n-trace metal layer 32 formed over the ohmic n-contact 30. The ohmic n-contact 30 may be, for example, a V/Al/Ti multilayer contact. The n-trace metal 32 may be, for example, a Ti/Au/Ti multi-layer contact.

The n-contact 28 and the p-contact 24 are electrically isolated by a dielectric layer 34. Dielectric layer 34 may be any suitable material such as, for example, one or more oxides of silicon, and/or one or more nitrides of silicon, formed by any suitable method. Dielectric layer 34 covers n-contact 28. Openings formed in dielectric layer 34 expose p-contact 24.

A p-trace metal 36 is formed over the top surface of the device, and substantially conformally covers the entire top surface. The p-trace metal 36 electrically connects to the p-contact 24 in the openings formed in dielectric layer 34. The p-trace metal 36 is electrically isolated from n-contact 28 by dielectric layer 34.

Robust metal pads terminating the p-trace metal 36 and n-contact 28 are provided outside of the drawing for connection to power supply terminals. The array of UV LEDs may be mounted on a support substrate, such as a printed circuit board, which may have an electrical pattern for connection to a power source. Other circuits may also be mounted on the printed circuit board.

A single UV LED 12 may be made any size to emit a desired optical power.

The remaining figures illustrate various examples of systems that make use of the UV LEDs 12 to achieve various functions, such as the detection of particles (including microorganisms) and the disinfection of mediums.

Detecting Particles in Air and Disinfecting the Air

Figure 3A:
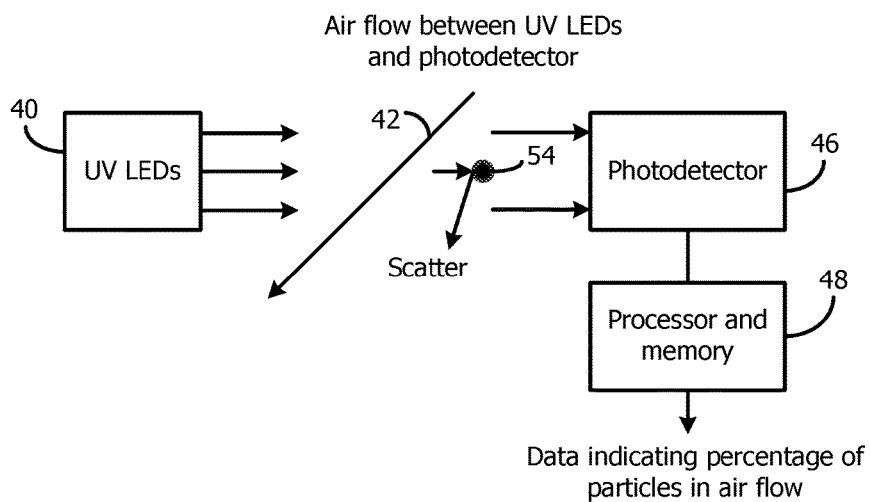
FIG. 3A illustrates a particle detection and disinfection system for an air duct.

FIG. 3A illustrates a system that detects particles in an air flow, or in a sample of air, and optionally disinfects the air to kill microorganisms. The system may be located in an air duct.

A UV source 40 that contains UVB and/or UVC LEDs directs UV light through an air stream or a static sample of air 42. The air 42 may be restricted in a chamber. The UV source 40 may output a wide emission using a two-dimensional array of UV LEDs so that a relatively large volume of air is analyzed for each sample. Alternately, the UV source 40 may generate a narrower beam and sample a smaller volume of air.

The air 42 may be prior to or after being filtered by a suitable porous filter. It is known to use visible light to determine attenuation by scattering or absorbing particles in air; however, the relatively long wavelengths of such light are not scattered or absorbed by very small particles on the order of the UV wavelength. Practical porous filters can filter out larger sizes of particles but cannot filter out such very small particles. The UV light has a wavelength that is much smaller than that of visible light, so the light can be scattered and/or absorbed by very small particles in post-filtered air. Such scattering or absorption attenuates the UV light that is detected by a photodetector 46 sensitive to the UV light. The system is controlled by a programmed processor and memory unit 48. Any other suitable controller may be used in all embodiments, such as a state machine.

Figure 3B:
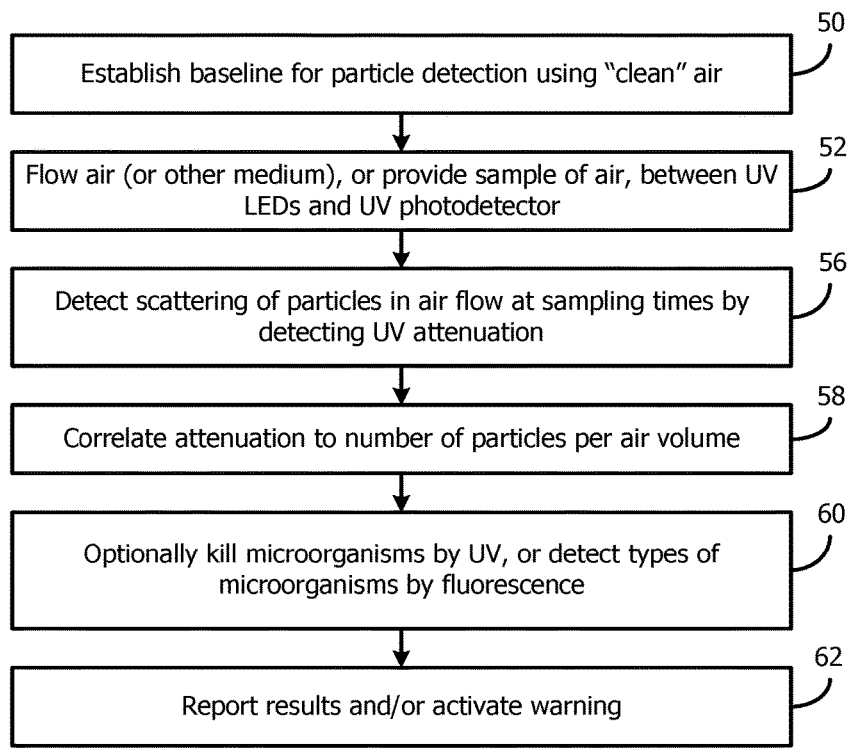
FIG. 3B is a flowchart describing the use of the system of FIG. 3A.

The process of FIG. 3B is used to detect particles in the air flow and optionally disinfect the air.

In step 50, the system is calibrated to establish a baseline, which represents a signal by the photodetector 46 representing 100% clean air. This may be done by testing a closed system in a controlled environment. Such baseline data is stored in the memory.

In step 52, the air to be analyzed is flowed between the UV source 40 and the photodetector 46. Alternatively, a portion of an air flow is periodically captured in a sampling enclosure containing the UV source 40 and the photodetector 46. In the example of FIG. 3A, some of the UV light is scattered by a particle 54, such as dust or a microorganism, and this light is absorbed by the walls of the chamber or by the particle 54 itself.

In step 56, the amount of UV light that is detected by the photodetector 46 over a unit of time is detected and compared to the baseline. The difference is the attenuation of UV light due to the light being scattered or absorbed.

In step 58, the processor correlates the measured attenuation to the number of particles (or other characteristic about the particles) per air volume to generate relatable data, such as the percentage of particles in the air. The data is periodically output for further analysis.

At the same time, in step 60, the UVB or UVC light kills the microorganisms in the air. Some microorganisms and compounds fluoresce in UV light, and this fluorescence may also be detected by the photodetector 46 or other detector and presented in the data. Thus, there is synergy in the UV light detecting very small post-filtered particles and the same UV light killing microorganisms and/or causing fluorescence of the particles.

In step 62, the results are reported and a warning may be activated if the data indicates a dangerous level of particles in the air.

UV Source Emitting Multiple Peak Wavelengths for Targeting Specific Microorganisms Research has identified the specific wavelengths that are most effective in killing certain common microorganisms. These wavelengths are typically in the range of 240 nm-280 nm, which is in the UVC range. For example, the bacteria anthrax is most efficiently killed with a wavelength of about 253-254 nm. Other microorganisms are most efficiently killed with other narrow ranges of wavelengths in the UVC range.

The prior art uses a very wide band UV emitter, comprising a gas within a vacuum tube energized with a high voltage, to perform such detection or disinfection. The vast majority of the optical power emitted by such a wide band emitter is wasted energy. Such a high power of UV light can be dangerous to humans over a prolonged period.

FIG. 4A illustrates a detection and disinfection system that outputs a plurality of very narrow ranges of UV wavelengths for killing selected types of microorganisms. There is little wasted optical energy since all of the wavelengths are calculated to achieve a specific function. Generally, an energy savings of over 90% can be achieved versus using a wide band UV emitter.

In the generally arbitrary example of FIG. 4A, five different types of UV LEDs 12 are housed in a reflective housing 70 that has a light exit opening for directing the light to a wide band photodetector 72. The peak wavelengths of 253 nm and 293 nm are known to be very effective for disinfection. The medium to be disinfected is shown as air 73, but any other medium, such as water, can be similarly disinfected. The emitted light for each wavelength may be a broad beam or a narrow beam. The UV LEDs 12 may be formed in a two-dimensional array, and the number of UV LEDs 12 of each type is determined based on the required optical power needed.

Although all the UV LEDS 12 may be energized at once, there is a benefit in sequentially energizing the UV LEDs 12, using the multiplexer 74, to obtain information relating to each peak wavelength. For example, some wavelengths cause a particular type of microorganism to fluoresce, and such fluorescence is detected by the photodetector 72. Also, some microorganisms absorb only a narrow wavelength of UV light, and such absorption (relative to a baseline) can be detected by the photodetector 72 in conjunction with the processor and memory unit 76.

FIG. 4B illustrates a method that may be performed by the system of FIG. 4A.

In step 80, the optimal UV peak wavelengths for killing or detecting the target microorganisms and/or compounds are determined. This can be done by simply researching existing papers on such optimal wavelengths.

In step 82, the UV LEDs that can emit such peak wavelengths are incorporated into the UV source 70.

In step 84, air or other medium is flowed between the UV source 70 and the photodetector 72.

In step 86, the different UV LEDs 12 are multiplexed so that the different wavelengths are emitted at different times. If required, certain wavelengths may be emitted for longer times than others. The photodetector 72 detects the optical power received for each wavelength. The processor 76 associates the output of the photodetector 72 with the wavelength, which also correlates to the targeted microorganism/compound.

In step 88, the processor 76 correlates the attenuation at each wavelength to the amount of absorption or scattering by the targeted microorganism/compound, which can be used to determine the quantity of the targeted microorganisms/compounds in the sample. The processor 76 may also correlates the fluorescence at each wavelength to the targeted microorganism/compound.

In step 90, the emitted UV also kills the targeted microorganisms.

In step 92, the results of the detection are reported. A warning is activated if appropriate.

Techniques for Coupling UV Light to a Medium

FIGS. 5-11 illustrate techniques to efficiently couple UV light generated by UV LEDs to air, water, or other flowing mediums. These techniques may be used in the systems of FIGS. 3 and 4.

Figure 5:
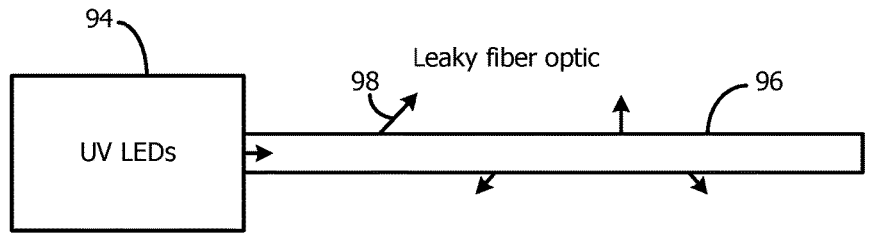
FIG. 5 illustrates a technique for emitting UV light along a leaky optical fiber.

FIG. 5 illustrates a UV source 94 containing UV LEDs. The UV light is emitted through a small opening and coupled to the end of an optical fiber 96. The fiber 96 is roughened along its length to evenly leak the UV light 98 over a wide angle.

Figure 6:
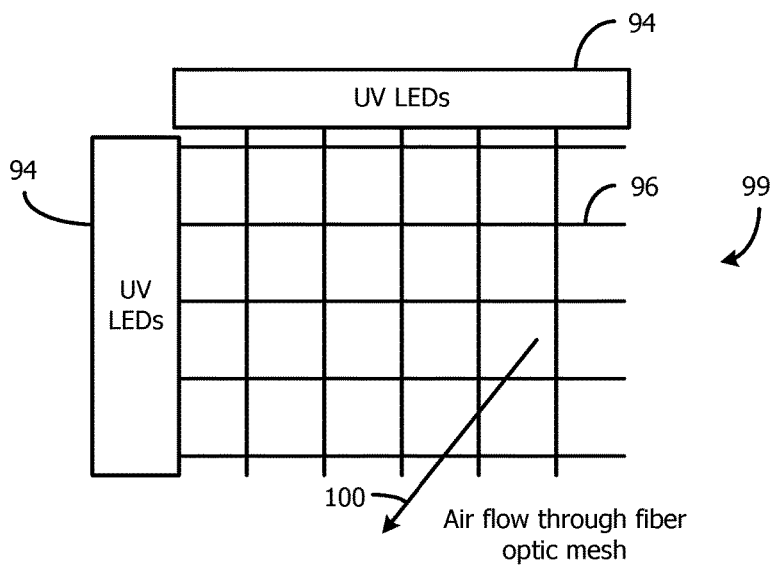
FIG. 6 illustrates how the optical fiber of FIG. 5 may form a mesh for coupling UV light to a medium flowing through the mesh.

FIG. 6 illustrates multiple fibers 98, each emitting UV light, configured as a mesh 99, with openings to allow the air 100 or water to pass through. The mesh 99 can be any size. The configuration enables the air or water to be exposed to UV light from all directions, maximizing the exposure.

Figure 7:
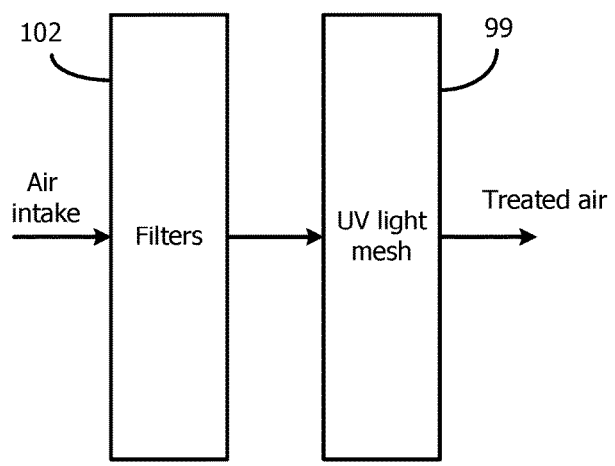
FIG. 7 illustrates the preferred location of the mesh relative to an air filter.

FIG. 7 illustrates how the mesh 99 may be positioned downstream from an air filter 102 so most particles are already removed from the air and only small particles and microorganisms remain.

FIG. 8 illustrates a thin, edge-lit, light guide 104 having an array of holes 106 through which air 100 or water flows. The light guide 104 is positioned in the path of the air or water. The hole sidewalls intercept the UV light in the light guide 104 and cause UV light to be emitted in the holes 106. The UV source 94, containing UV LEDs, is coupled to the edge of the light guide 104, which may be a transparent acrylic sheet or other transparent polymer. The light guide 104 surfaces may be roughened to leak the UV light over its surfaces to further expose the air 100 to UV light.

FIG. 9 illustrates how the UV LEDs 12 can be mounted as an array on a circuit board 108. Air or water is then passed in front of the circuit board 108 to expose the air/water to the UV light 109.

FIG. 10 illustrates how a light guide 110, such as an acrylic sheet, may be edge-lit by UV LEDs in the UV source 94, and the surfaces of the light guide 110 are roughened to leak out the UV light 111. Air or water is then passed in front of the light guide 110 to expose the air/water to the UV light. The UV emission may be bidirectional.

FIG. 11 illustrates how the circuit boards 108 or light guides 110 (panels) may be positioned in an air/water flow to channel the air/water for maximum exposure. By placing a large number of the panels close together, the flowing medium is exposed to a high level of UV for an extended time.

Typically, LEDs are driven by a current regulator (a power converter) that receives an unregulated input voltage. FIG. 12 illustrates how the UV source 94, containing any number of UV LEDs, can be connected to a power converter 114 via a flex-cable 116 (or other form of flexible conductor), where the input voltage Vin may be supplied via wires to the power converter 114. Since the power converter 114 regulates the current, it should be fairly close to the UV LEDs to limit the resistance of the flex-cable 116. However, the wires conducting Vin may be long since the power converter 114 will compensate for any voltage drop along such wires. By using the flex-cable 116, the power converter 114 may be located in an optimal location.

Medical Applications of UV LEDs

It is known to use a wide bandwidth germicidal UV lamp during surgery to kill bacteria. However, only a small part of the wavelength is effective in killing the targeted bacteria, such as a wavelength about 200 nm. The vast majority of the wavelengths is not performing any useful function and can be dangerous to the patient. The optimal UV emitter is one that emits only at the optimal wavelengths, such as around 200 nm, and where the UV light is directed only to the area of interest.

In microsurgery, two or three small holes are formed in the patient, and the operation is carried out using narrow tools entering the patient's body through the holes.

Figure 13:
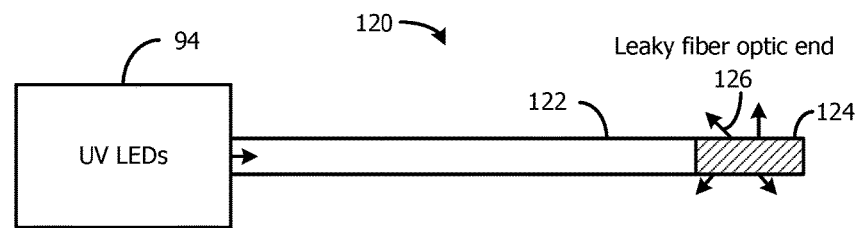
FIG. 13 illustrates a tool that may be used in microsurgery to disinfect an area inside the patient's body.

FIG. 13 illustrates a disinfection tool 120 for killing bacteria during microsurgery. A UV source 94 contains one or more UV LEDs emitting the wavelengths of interest. The UV source 94 may comprise a reflective chamber having a small exit window through which all UV light exits. The UV light is coupled to the end of an optical fiber 122, whose end area 124 is roughened to leak out all the UV light 126. The thickness of the fiber 122 may be on the order of 25 microns. The surgeon inserts the fiber 122 into one of the holes in the patient for disinfecting only the area in which the surgeon is operating using microsurgery. The UV source 94 may also contain white light LEDs or other visible-light LED for illuminating the target area within the patient during surgery. The fiber 112 may be coated with any suitable material for safety. Killing harmful bacteria is particularly important during operations on the stomach, intestines, bladder, kidney, and liver.

Figure 14:
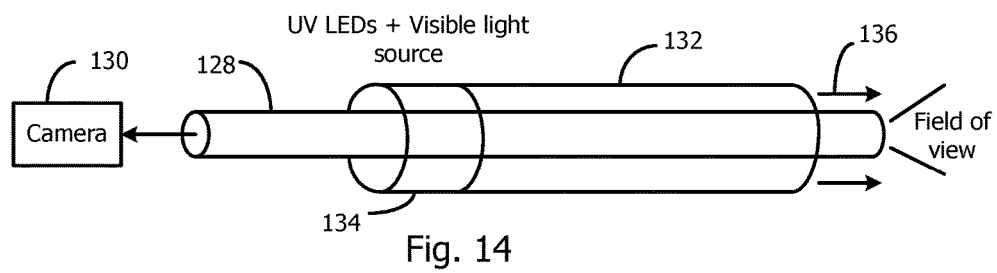
FIG. 14 illustrates how UV and visible light may be coupled to a flexible optical fiber to deliver the light to an area inside a patient's body for disinfection and to view the area with a remote camera.

FIG. 14 illustrates how a center optical fiber 128 may be used to optically couple an image received at one end of the fiber 128 to a video camera 130 at the other end during microsurgery. To provide illumination and disinfection during the surgery, an outer transparent optical layer 132 is coaxial with the fiber 128. Both UV (e.g., peak wavelength at 200 nm) and visible light from a light source 134 are optically coupled to one end of the optical layer 132, and this light 136 leaks out the opposite end of the optical layer 132 to illuminate and sanitize the surgical area. For example, the small LEDs (less than 1 mm in width) may be directly facing the end of the optical layer 132 for coupling light into the optical layer 132. The tool may be thin (less than 0.5 cm) and flexible, allowing it to be inserted into a small hole in a patient's body during microsurgery.

Additionally, it may be useful to inject a liquid containing nanoparticles of an inorganic phosphor into the bloodstream and learn about the patient's body by viewing the locations of the nanoparticles in the body. The tool of FIG. 14 may be used to energize and observe the phosphor at particular locations. The visible light LEDs may be turned off.

Techniques for Directly Coupling UV Light into a Water Stream for Disinfecting a Surface It is known that certain wavelengths of UV light kill mold and other microorganisms that grow on food, and the UV light extends the shelf life of such food. However, constantly exposing the food to the UV light is not efficient and may impose a danger.

Figure 15:
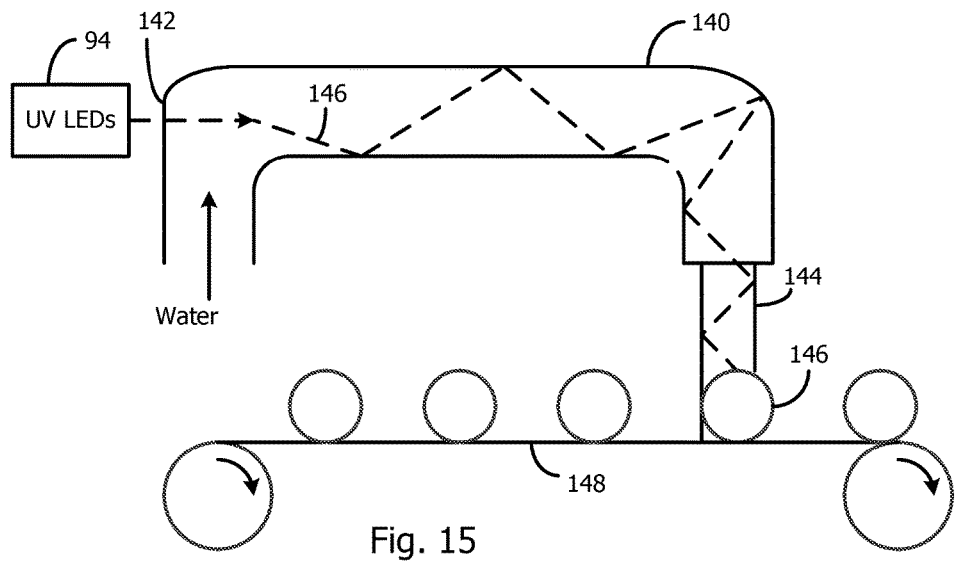
FIG. 15 illustrates how the UV light may use a stream of water as a light guide to delivery UV light to the surface of food for disinfection.

Food is typically washed with water during processing. A contiguous stream of water acts like a light guide. FIG. 15 illustrates a simplified washing system that directly couples the UV light to the surface of the food for maximum UV exposure. A pipe 140 has a transparent window 142 through which UV light from a UV source 94, containing UV LEDs, is coupled to a stream of water 144. The UV light 146 is shown being reflected within the stream of water 144 inside and outside of the pipe 140. The water "containing" the UV light is used to clean and disinfect the food 146, such as vegetables and fruit, on a conveyor belt 148. Such washing may also be periodically performed while the food is being displayed. Other types of water cleaning systems may also be used. Even if the stream of water breaks up before contacting the food, such as with a spraying system, the UV light exiting the pipe 140 will still be directed toward the food.

Techniques to Disinfect Touched Surfaces

There are many surfaces that are touched by the public, and germs are spread to others via such touching. Such surfaces include light switches, door handles, ATM keypads, keyboards, touch screens, fingerprint readers, elevator buttons, etc. Rather than simply exposing the touched surfaces to externally-generated UV light, the following techniques integrate UV LEDs into such systems.

FIG. 16 illustrates a light switch module 150 having a lever 152 that is toggled to turn on or off a light, represented as a load 154. The switch module 150 has terminals that are connected to ground (or neutral) and a hot lead. UV LEDs 156, emitting wavelengths that are optimal for killing the target microorganisms, are located within the switch module 150 and receive power by either a separate power supply or the voltage difference that is present across the switch module terminals when the switch is off. The UV LEDs are naturally only activated when the switch is off, since the UV LED electrodes are effectively shorted together when the switch is on. This is good for safety since the UV light should not contact skin. The lever 152 is a translucent plastic and leaks the UV light to disinfect the outside surface of the lever 152.

To visually indicate that the UV LEDs 156 are on, the lever 152 may be coated with a phosphor or a fluorescent material that emits a visible light 157 when energized by UV light 158. Thus, the glowing lever 152 serves to identify the position of the lever 152 in the dark.

This same technique of employing UV LEDs within a structure to cause light to leak out a touched surface can be applied to many other systems that are touched. For example, a translucent door knob system may employ powered UV LEDs within the system to expose the outer surface of the door knob to UV light. In such an embodiment, the UV LEDs may be located within the translucent door knob itself along with a battery so the door knob can replace a standard metal door knob.

FIG. 17A illustrates a fingerprint scanner 160 that images a user's fingerprint (on the tip of finger 162) using a digital imager 164. In prior art fingerprint scanners, such as used in airports for security, all passengers of a plane may touch the same glass surface for imaging and recording their fingerprints. The operator may decide to periodically sanitize the glass surface by wiping with a towel. However, germs have already been spread to the passengers that have used the fingerprint scanner.

In FIG. 17A, the light from a UV source 166, containing UV LEDs, is coupled to the edge of a glass plate 168 that is touched when providing a fingerprint. The glass plate 168 acts as a leaky light guide for the UV light for disinfecting the surface after each fingerprint scan. Alternatively, the UV source 166 may be located below the glass plate 168 and is emitted through the top surface of the glass plate 168. The imager 164 senses when a finger 162 has been removed from the glass plate 168, and a processor 170 controls a power supply 172 to energize the UV LEDs for a time (e.g., 2 seconds) when there is no finger on the glass plate 168.

Since UV light may damage skin, safety precautions may be used. When the UV LEDs are energized, visible light LEDs in the source 166 are also energized and the visible light is coupled to the glass plate 168 (or illuminated below the glass plate 168) so the operator can visually see when the UV LEDs are on. Alternatively, no visible light LEDs are used, but a phosphor layer 174 on the glass plate 168 emits visible light when energized by UV light and provides the indication that the UV LEDs are energized. An exposure of the surface of the glass plate 168 for a second or two may be sufficient to sanitize the glass surface after each fingerprint scan.

FIG. 17B summarizes the operation of the fingerprint scanner. In step 176, the processor 170 detects that no finger is touching the glass plate 168.

In step 178, the UV and visible LEDs (if used) are automatically briefly turned on to disinfect the glass surface. In step 180, the next fingerprint scan is performed, and the process repeats.

FIG. 18A illustrates a conventional capacitive touch screen layer 182 overlying a liquid crystal display (LCD) screen 184. The LCD screen 184 is backlit with a backlight 186. The touch screen detects the XY position of a fingertip touch, and the XY position is correlated, via a processor, to a function to be performed. The touch screen layer 182 is transparent and may be a glass or plastic plate supporting the XY sensors (e.g., semi-transparent conductor areas). A UV source 188, containing UV LEDs emitting optimal wavelengths for killing target microorganisms, emits UV light that is optically coupled to the edge of the touch screen layer 182. The touch screen layer 182 is typically translucent enough (due to the semi-transparent conductors) to act as a leaky light guide to expose the surface to the UV light. The surface may be roughened to increase the light emission. The UV LEDs are only energized when no touching is sensed or during pre-determined times.

A timer 190 controls the exposure time, and a processor 192 controls the system.

Visible LEDs may also be included in the source 188 and are energized along with the UV LEDs as a visual indicator that the UV LEDs are on.

FIG. 18B summarizes the operation of the touch screen disinfector. In step 194, the user sets the timing for the disinfecting, such as at a particular time of the evening, or after every 10 minutes, etc. The disinfecting may also be automatically performed after each touch.

In step 196, the UV and visible LEDs (if any) are energized and, in step 198, the UV light impinges on the surface of the leaky touch screen 182 to disinfect the surface.

FIG. 19A illustrates a system having translucent buttons 200, such as in an elevator or a keyboard/keypad, where the UV light from a UV source 202, containing UV LEDs, is coupled to the edge of a backlight 204 along with visible light, such as from white light LEDs in the source 202. The backlight 204 is leaky to emit all light in the direction of the translucent buttons 200. Pushing a button 200 is sensed by a processor 206 for carrying out the desired function. A timer 208 turns on the UV LEDs in the source 202 for a brief period, such as after each button press, to sanitize the buttons 200, whereby the outer surface of the buttons 200 is exposed to the UV light. The visible LEDs may be constantly on for the backlight 204.

In another embodiment, the backlight comprises a support surface, and the visible LEDs and UV LEDs are distributed over the support surface for directly illuminating the back of the buttons 200.

FIG. 19B summarizes the operation of the disinfection system of FIG. 19A. In step 210, the operator sets the desired timing of the UV LEDs for disinfection, such as at a certain time, or every 10 minutes, or after each button press.

In step 212, the white light LEDs are continually energized for backlighting the transparent buttons 200.

In step 214, the UV LEDs are periodically energized to disinfect the buttons 200.

Figure 20A:
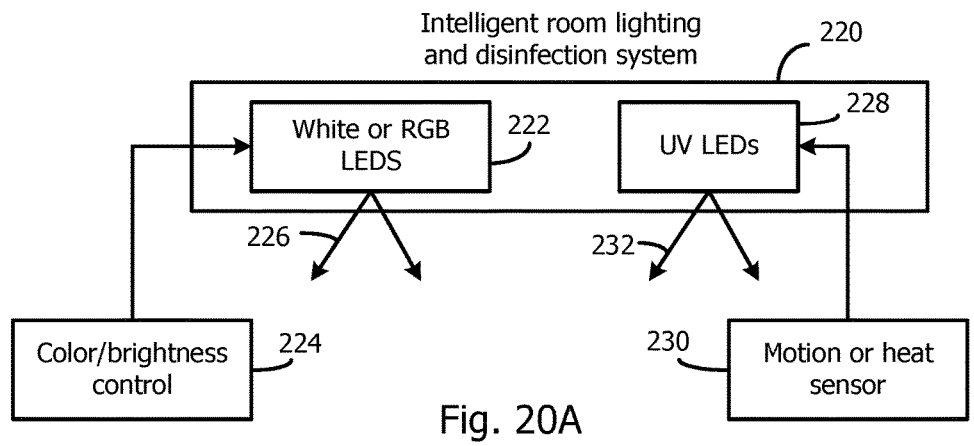
FIG. 20A illustrates a general lighting system that also includes UV LEDs for disinfecting surfaces and the air.

General Lighting System Having Integrated UV LEDs for Disinfecting Air and Surfaces In public places, such as schoolrooms, hospitals, buses, stations, offices, etc., both the air and touched surfaces are ideally sanitized periodically to kill microorganisms. FIG. 20A is an intelligent general lighting system using both visible light LEDs and UV LEDs to provide general illumination along with disinfection.

A luminaire 220 of any design is typically supported by the ceiling of a room. The luminaire 220 contains white light LEDs 222 or red, green, and blue LEDs for creating white light. These LEDs 222 may be controlled by a color/brightness controller 224 for illuminating the room with white light 226. Since UV light may be dangerous with prolonged exposure, the UV LEDs 228 are only energized when there is no person in the room. This may be detected by a motion or heat sensor 230. The UV wavelengths are selected to be optimal for killing the target microorganisms on surfaces and in the air. The UV light 232 may be emitted toward the ceiling and downward. The upward UV light may be emitted constantly if there is no dangerous downward reflection of the UV light.

Figure 20B:
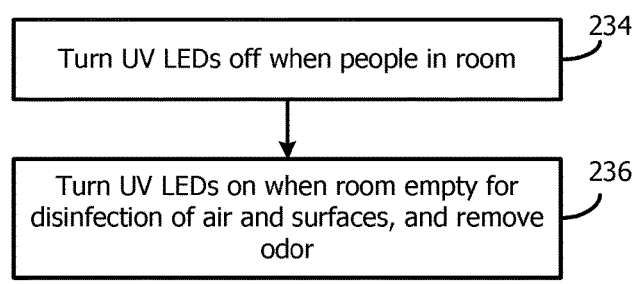
FIG. 20B is a flowchart describing the use of the system of FIG. 20A.

FIG. 20B summarizes the operation of the disinfection system of FIG. 20A. In step 234, the UV LEDs are turned off when there are people detected being in the room and, in step 236, the UV LEDs are turned on when the room is empty to disinfect the air and surfaces and remove odors cause by microorganisms.

UV LEDs Used for Skin Treatment

UV light of particular wavelengths is known to mitigate various skin conditions and generate vitamin D.

Figure 21:
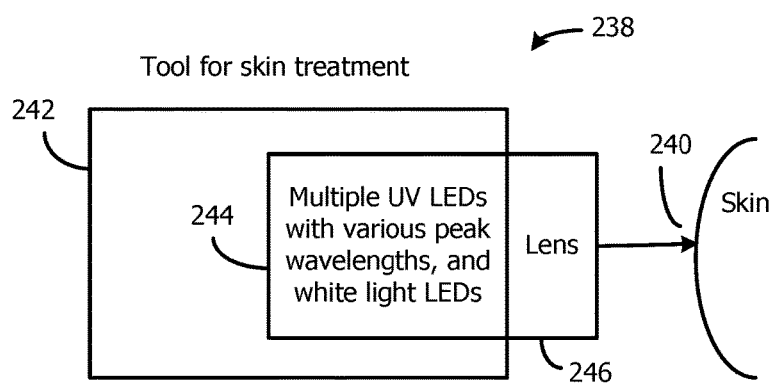
FIG. 21 illustrates a system for focusing UV light onto skin.

FIG. 21 illustrates a tool 238 used by dermatologists that focuses UV light only on the small skin area 240 to be treated. In this way, there is no damage to other areas. The tool 238 includes a handle 242, UV LEDs and visible light LEDs in a source 244, and an optional lens 246 for focusing the light. The visible light LEDs are energized along with the UV LEDs to illuminate the skin surface while also indicating that the UV LEDs are energized.

FIG. 22 illustrates a resilient wristband 250 worn on the wrist or ankle. The outer surface may be opaque and have a reflective inner surface. One or more UV LEDs 252, emitting optimal wavelengths for generating vitamin D, are integrated into the wristband 250 to couple the UV light into a transparent or translucent inner layer 254 of the wristband 250. Alternatively, the UV LEDs may be distributed around the wristband 250. A battery power source and any controller are integrated with the UV LEDs within the layer 250. A low power, but long, exposure of the skin to the UV light safely creates vitamin D in the blood stream, which is carried to other parts of the body. Wearing the wristband 250 on the wrist is optimal due to the proximity of major arteries and large veins to the skin surface. The battery may be recharged using inductive coupling. An on/off switch may be provided or a sensor automatically determines that the wristband 250 is being worn.

FIG. 23A illustrates a bottle of skin lotion 256, such as for treatment of a skin ailment or a sun screen. The lotion 256 contains inert nanoparticles of a phosphor or fluorescent material that are uniformly suspended in the lotion 256. The proper coverage of the lotion 256 on a person's skin is verified by illuminating the treated area with UV light from a UV source 258 containing UV LEDs. The nanoparticles in the applied lotion will provide a visual indication of the location of the lotion 256 on the body.

The invention also applies to suspending phosphor nanoparticles in any liquid that is to be spread on a surface, including clear varnishes, waterproofing treatments, etc.

The operation of the system of FIG. 23A is summarized in FIG. 23B. In step 260, the liquid containing the nanoparticles (e.g., lotion 256) is spread on a surface, such as skin. In step 262, the UV LEDs are energized and the UV light is directed to the surface to cause the nanoparticles to emit visible light for detecting the proper coverage on the surface.

In all cases, although UV LEDs emit a narrow band of wavelengths with a peak wavelength, it may be desired to further narrow the bandwidth. This may be done with a multi-layer Bragg filter or other type of optical filter.

Many variations of the above-described techniques of FIGS. 3-23 are envisioned, and the techniques would be customized for each particular application. Elements from the various embodiments may be combined as needed for a particular application.

While particular embodiments of the present invention have been shown and described, it will be obvious to those skilled in the art that changes and modifications may be made without departing from this invention in its broader aspects and, therefore, the appended claims are to encompass within their scope all such changes and modifications as fall within the true spirit and scope of this invention.

What is claimed is:

1. A combined disinfection and lighting luminaire comprising:
   a first set of light emitting diodes (LEDs), a second set of LEDs, and a third set of LEDs, the first, second, and third sets of LEDs being housed in a single luminaire;

the first set of LEDs generating a first light for producing white light to illuminate a room when energized;

the second set of LEDs generating invisible light in the UV range, wherein UV light from the second set of LEDs is directed downward to disinfect surfaces in the room when energized;

the third set of LEDs generating invisible light in the UV range, wherein UV light from the third set of LEDs is not directed downward, and wherein the UV light from the third set of LEDs is for disinfecting air in the room when energized;

a sensor in the luminaire for detecting whether there are people in the vicinity of the luminaire, wherein the sensor is coupled to automatically control at least the second set of LEDs; and the luminaire being configured to operate in at least two modes wherein, the luminaire being operable in a first mode, when the sensor detects a person is in the vicinity of the luminaire, in which the second set of LEDs automatically ceases to emit the downward light, while the third set of LEDs remains energized to disinfect the air, the luminaire being operable in a second mode, when the sensor detects no people in the vicinity of the luminaire, in which both the second set of LEDs and the third set of LEDs are energized to disinfect surfaces in the room and disinfect air in the room.

2. The luminaire of claim 1 further comprising a wavelength conversion material for converting the first light from the first set of LEDs to a longer wavelength to produce the white light.

3. The luminaire of claim 1 wherein the first set of LEDs comprise red, green, and blue light emitting LEDs to produce the white light.

4. The luminaire of claim 1 wherein the invisible light generated by the second and third sets of LEDs is in at least the UVC range.

5. The luminaire of claim 1 wherein the sensor senses motion in the room.

6. The luminaire of claim 1 wherein the sensor senses heat from a person in the room.

7. The luminaire of claim 1 wherein a controller controls a brightness of the first set of LEDs independent of the second set of LEDs.

8. The luminaire of claim 1 wherein the UV range is selected to kill target microorganisms on the surfaces in the room and in the air in the room.

9. The luminaire of claim 1 wherein the third set of LEDs illuminates a ceiling in the room.

10. The luminaire of claim 1 wherein the luminaire is controlled so that the third set of LEDs is always on when the first set of LEDs is on.

11. A method for selective illumination and disinfection of a room by a luminaire, the luminaire containing a first set of light emitting diodes (LEDs), a second set of LEDs, and a third set of LEDs, the first set of LEDs generating a first light for producing white light to illuminate the room when energized, the second set of LEDs generating invisible light in the UV range wherein light from the second set of LEDs is directed downward to disinfect surfaces in the room when energized, and the third set of LEDs generating invisible light in the UV range to disinfect air in the room when energized, the light from the third set of LEDs not being directed downward, the method comprising:

controlling the first set of LEDs to be energized for generating a first light for producing white light to illuminate the room;

sensing, via a sensor in the luminaire, whether there are people in the vicinity of the luminaire;

in response to sensing that there are people in the vicinity of the luminaire, automatically controlling the second set of LEDs to be off while the third set of LEDs remains on to disinfect the air irrespective of whether there are people in the vicinity of the luminaire; and in response to sensing that there are no people in the vicinity of the luminaire, automatically controlling the second set of LEDs to be on while the third set of LEDs remains on to disinfect the air irrespective of whether there are people in the vicinity of the luminaire.

12. The method of claim 11 wherein the invisible light is in at least the UVC range.

13. The method of claim 11 wherein the sensor senses motion in the room.

14. The method of claim 11 wherein the sensor senses heat from a person in the room.

15. The method of claim 11 wherein the UV range is selected to kill target microorganisms on surfaces in the room and in the air in the room.

16. The method of claim 11 wherein the third set of LEDs illuminates a ceiling in the room.

17. The method of claim 11 wherein the first set of LEDs is controlled independently from the second set of LEDs.

* * * * *